(12) United States Patent
Pugh et al.

(10) Patent No.: US 10,252,038 B2
(45) Date of Patent: Apr. 9, 2019

(54) FLUID DELIVERY DEVICE FOR THE NASAL CAVITY

(71) Applicant: Neosinus Health LLC, Raleigh, NC (US)

(72) Inventors: Magda R. Pugh, Raleigh, NC (US); Kashif Mazhar, Raleigh, NC (US)

(73) Assignee: Neosinus Health LLC, Raleigh, NC (US)

( * ) Notice: Subject to any disclaimer, the term of this patent is extended or adjusted under 35 U.S.C. 154(b) by 896 days.

(21) Appl. No.: 14/617,188

(22) Filed: Feb. 9, 2015

(65) Prior Publication Data

US 2016/0228685 A1    Aug. 11, 2016

(51) Int. Cl.
| | | |
|---|---|---|
| *A61M 31/00* | (2006.01) | |
| *A61H 35/04* | (2006.01) | |
| *A61M 3/02* | (2006.01) | |
| *A61M 25/00* | (2006.01) | |

(52) U.S. Cl.
CPC .............. *A61M 31/00* (2013.01); *A61H 35/04* (2013.01); *A61M 3/0279* (2013.01); *A61M 25/007* (2013.01); *A61M 25/0068* (2013.01); *A61M 2025/0004* (2013.01); *A61M 2025/0008* (2013.01); *A61M 2210/0618* (2013.01)

(58) Field of Classification Search
CPC .. A61M 1/008; A61M 3/0262; A61M 3/0279; A61M 25/0026; A61M 25/0041; A61M 25/0068; A61M 25/007; A61M 2025/0008; A61M 2025/0039; A61M 2025/0681; A61M 31/00; A61M 2210/0618; A61B 17/88; A61H 35/04
See application file for complete search history.

(56) References Cited

U.S. PATENT DOCUMENTS

| | | | | |
|---|---|---|---|---|
| 4,444,560 | A | * | 4/1984 | Jacklich ............ A61M 5/31595 222/391 |
| 5,244,458 | A | * | 9/1993 | Takasu ................ A61M 1/0056 604/22 |
| 5,935,098 | A | * | 8/1999 | Blaisdell ................... A61F 6/18 604/103.01 |
| 2006/0210605 | A1 | * | 9/2006 | Chang ..................... A61B 17/24 424/434 |

(Continued)

FOREIGN PATENT DOCUMENTS

WO    WO 2009049823 A1 * 4/2009    ........ A61M 25/0009

*Primary Examiner* — Bhisma Mehta
*Assistant Examiner* — Larry R Wilson
(74) *Attorney, Agent, or Firm* — Coats & Bennett, PLLC

(57) ABSTRACT

A device for delivering fluid to a nasal cavity comprises an elongated member comprising a hollow exterior cannula and a hollow interior cannula. The interior cannula is flexible, is at least partially housed within the exterior cannula, and comprises an inlet for intake of the fluid and at least one outlet for ejecting the fluid. The exterior cannula has outlets for ejecting the fluid which are positioned within the nasal cavity by inserting the distal end of the device through a given nostril. A portion of the device has a continuously curving centerline that divides the device into a first and second lateral section. At least one outlet is positioned in each of the first and second lateral sections. Rotation of the distal section of the interior cannula within the exterior cannula permits the ejection of fluid predominantly out of outlets on respective lateral sides of the outer cannula.

14 Claims, 12 Drawing Sheets

(56) References Cited

U.S. PATENT DOCUMENTS

| | | | | |
|---|---|---|---|---|
| 2008/0125746 | A1* | 5/2008 | Shapland | A61M 25/10 604/508 |
| 2009/0198216 | A1* | 8/2009 | Muni | A61B 17/24 604/514 |
| 2013/0274711 | A1* | 10/2013 | O'Day | A61M 5/16813 604/508 |
| 2014/0276656 | A1* | 9/2014 | Bian | A61M 27/00 604/541 |

* cited by examiner

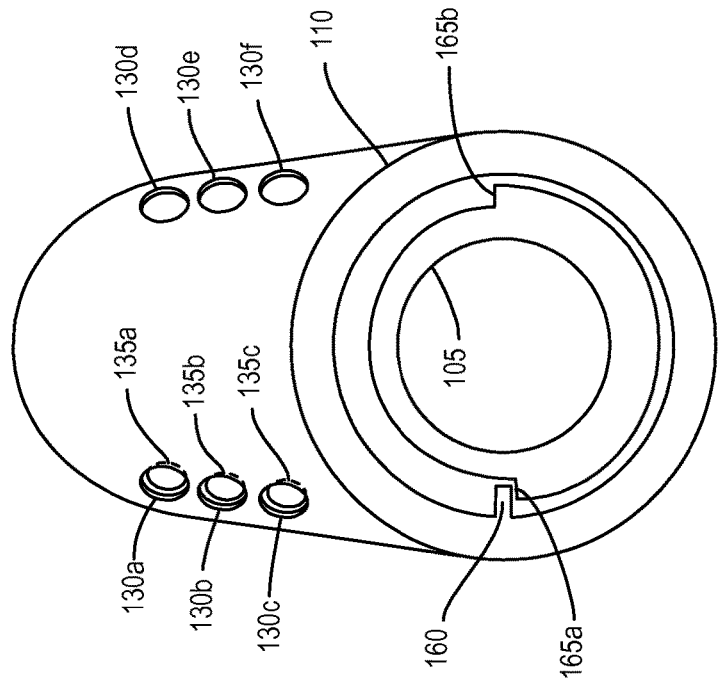
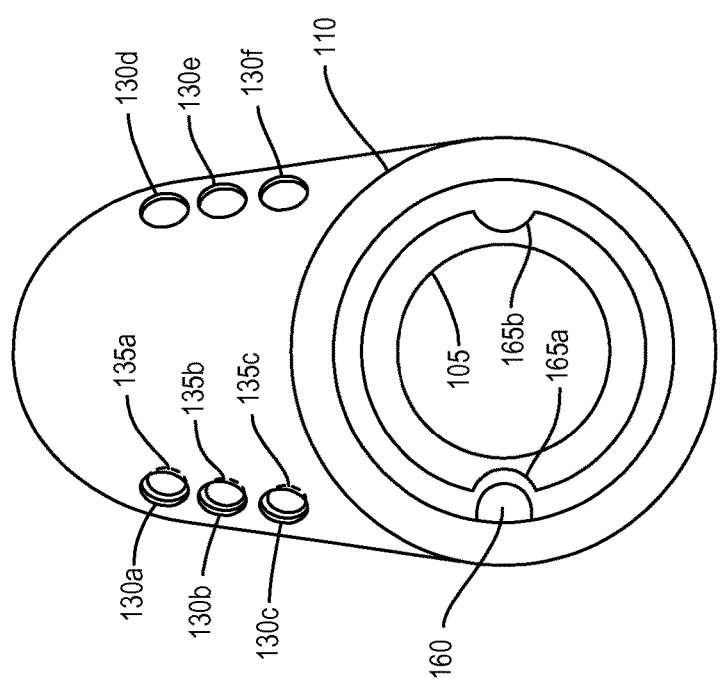

FLUID DELIVERY DEVICE FOR THE NASAL CAVITY

TECHNICAL FIELD

The present disclosure relates to delivering fluid to the nasal cavity using a delivery device, and more particularly to the efficient and targeted delivery of therapeutic fluids, including medication, to specific turbinates and/or sinuses within the nasal cavity.

BACKGROUND

The nasal cavity comprises a variety of surfaces that correspond to anatomic structures serving various respective biological functions. Generally, the nasal cavity is divided vertically by a wall of cartilage called the septum. On each side of the septum is a nostril through which the nasal cavity can be accessed. Opposite the septum, on each lateral side of the nasal cavity, are a series of turbinates (also known as concha). Each series comprises an inferior, middle, and superior turbinate, as one goes backward from the nostrils, through the nasal cavity, towards the throat. These turbinates are a series of bony ridges that protrude into the nasal cavity. The maxillary, anterior ethmoid, and frontal sinuses drain into the nasal cavity from under the middle turbinate, which is above the inferior turbinate.

In order to treat these anatomic structures within the nose, therapeutic fluids can be topically applied to their corresponding surfaces. Such fluids for example, include saline, antihistamines, decongestants, and corticosteroids, which may be helpful in irrigating nasal passages, treating allergies, relieving nasal congestion, and treating inflammation, respectively. To deliver these fluids to various surfaces in the nasal cavity, a spray bottle is often used. To use the spray bottle, a patient typically inserts a nozzle through their nostril and ejects fluid from the nozzle in a haphazard and indiscriminate fashion. While haphazardly and indiscriminately dispensing fluid in this fashion tends to result in at least some fluid being applied to an appropriate surface within the nasal cavity, such an approach is inefficient at best. Indeed, a large percentage of the fluid delivered by this method is often wasted by being applied to surfaces for which the fluid can deliver little to no therapeutic value.

SUMMARY

Embodiments of the present disclosure generally relate to a fluid delivery device for the nasal cavity. In particular, the fluid delivery device is capable of targeting particular structures within the nasal cavity in order to efficiently deliver fluid.

Exemplary embodiments of the disclosure comprise a device for delivering fluid to a nasal cavity. The device comprises an elongated member comprising a hollow exterior cannula and a hollow interior cannula. The elongated member including a proximal section that extends inward from a proximal end and a distal section that extends from the proximal section to a distal end. The interior cannula is housed within the exterior cannula throughout the distal section. The distal section has a centerline comprising a curve that extends in a plane dividing the distal section into a first lateral section and a second lateral section. The interior cannula includes an inlet at the proximal end in fluid-flow relationship to a first outlet along the distal section. The first outlet opens into the exterior cannula. The exterior cannula includes, along the distal section, a second outlet having a center in the first lateral section, and a third outlet having a center in the second lateral section. The first outlet is selectively positionable into a first and second orientation by rotation of the distal section of the interior cannula within the exterior cannula. The first orientation comprises the first outlet in closer proximity to the second outlet than to the third outlet, thereby permitting fluid ejected from the first outlet to be predominantly ejected out of the second outlet relative to the third outlet. The second orientation comprises the first outlet in closer proximity to the third outlet than to the second outlet, thereby permitting fluid ejected from the first outlet to be predominantly ejected out of the third outlet relative to the second outlet.

In some embodiments, the second outlet is positioned symmetrically to the third outlet with respect to the plane.

In some embodiments, the distal section is between three and five centimeters long, and the curve has between sixty and eighty degrees of curvature. In an embodiment, the distal section is between 3.75 and 4.25 centimeters long, and the curve has between sixty-seven and seventy-three degrees of curvature.

In some embodiments, the distal section of the interior cannula is flexible relative to the exterior cannula to permit the rotation of the interior cannula within the exterior cannula, and such that the exterior cannula maintains the curve of the distal section during the rotation.

In some embodiments, the exterior cannula and interior cannula connect at a rotating joint such that the distal end of the interior cannula is kept centered within the distal end of the exterior cannula during the rotation of interior cannula within the exterior cannula.

In some embodiments, the interior cannula further comprises an alignment tab that protrudes from an exterior surface of the interior cannula, and the exterior cannula further comprises a first landing surface and a second landing surface. Upon rotation of the interior cannula to position the first outlet into the first orientation, the alignment tab contacts the first landing surface. Upon rotation of the interior cannula to position the first outlet into the second orientation, the alignment tab contacts the second landing surface.

In some embodiments, the exterior cannula further comprises an alignment tab that protrudes from an interior surface of the exterior cannula, and the interior cannula further comprises a first landing surface and a second landing surface. Upon rotation of the interior cannula to position the first outlet into the first orientation, the alignment tab contacts the first landing surface. Upon rotation of the interior cannula to position the first outlet into the second orientation, the alignment tab contacts the second landing surface.

In some embodiments, the device further comprises a depth stop, connected to the exterior cannula, for preventing more than the distal section from being inserted into the nasal cavity.

In some embodiments, the interior cannula further includes at least one fourth outlet, each fourth outlet opening into the exterior cannula and being in fluid-flow relationship with the inlet. The exterior cannula further includes at least one fifth outlet, each having a center in the first lateral section, and at least one sixth outlet, each having a center in the second lateral section. The first orientation further comprises each fourth outlet in closer proximity to a respective fifth outlet than a respective sixth outlet, thereby permitting fluid ejected from each fourth outlet to be predominantly ejected out of the respective fifth outlet relative to the respective sixth outlet. The second orientation further comprises each fourth outlet in closer proximity to a respective sixth outlet than a respective fifth outlet, thereby permitting fluid ejected from each fourth outlet to be predominantly ejected out of the respective sixth outlet relative to the respective fifth outlet.

In some embodiments, the interior cannula further includes a shaft connecting the distal section of the interior cannula to the inlet at the proximal end. In an embodiment, the shaft comprises a bend.

In some embodiments, the inlet comprises a mating adapter for mating with a fluid-dispensing source.

In some embodiments, the interior cannula further includes, at the distal end, a seventh outlet in fluid flow relationship to the inlet and opening into the exterior cannula. The exterior cannula further includes an eighth outlet at the distal end.

Other embodiments of the disclosure comprise methods of delivering fluid to a nasal cavity comprising a first set of turbinates corresponding to a first nostril and a second set of turbinates corresponding to a second nostril. Each set of turbinates comprise an inferior, middle, and superior turbinate. The first set of turbinates and first nostril are separated from the second set of turbinates and second nostril by a septum. The method comprises inserting an elongated cannula through a given nostril and into the nasal cavity in a first direction, thereby positioning a distal end of the cannula in the nasal cavity, a proximal end of the cannula exterior to the nasal cavity, and one or more outlets of a distribution section of the cannula in the nasal cavity, such that the one or more outlets predominantly face away from the septum and toward the set of turbinates corresponding to the given nostril, the distribution section of the cannula being positioned away from the distal end of the cannula. The method further comprises moving fluid into an inlet at the proximal end and along the cannula while the cannula is in the nasal cavity, and expelling fluid from the distribution section of the cannula in a direction predominantly transverse to the first direction thereby delivering the expelled fluid to at least one of the turbinates in the set of turbinates corresponding to the given nostril.

In some embodiments, the method further comprises expelling the fluid from the distal end of the cannula.

In some embodiments, the method further comprises preventing fluid from being expelled from the cannula towards the septum while fluid is being expelled from the distribution section.

In some embodiments, the method further comprises preventing fluid from being expelled from the distal end of the cannula while fluid is being expelled from the distribution section.

In some embodiments, delivering the expelled fluid to at least one of the turbinates in the set of turbinates corresponding to the given nostril comprises delivering the fluid predominantly to the middle turbinate, relative to the inferior and superior turbinates, corresponding to the given nostril.

Other embodiments comprise a device, having a proximal section that extends inward from a proximal end and a distal section that extends from the proximal section to a distal end, for delivering fluid to a nasal cavity. The device comprises a hollow interior cannula comprising an inlet at the proximal end and a first outlet positioned in the distal section, the inlet and the first outlet being in fluid-flow relationship. The device also comprises a hollow exterior cannula housing at least the distal section of the interior cannula. The exterior cannula comprises a second and third outlet in the distal section. The exterior cannula is also stiff relative to the distal section of the interior cannula. The second outlet is on a first lateral side of the exterior cannula. The third outlet is on a second lateral side of the exterior cannula, the second lateral side opposing the first lateral side. The distal section of the device has a centerline comprising a curve that extends in a plane dividing the first and second lateral sides. The first outlet is selectively positionable into a first and second orientation by rotation of the distal section of the interior cannula within the exterior cannula. The first orientation comprises the first outlet opening into the second outlet, thereby permitting fluid ejected from the first outlet to be predominantly ejected out of the second outlet relative to the third outlet. The second orientation comprises the first outlet opening into the third outlet, thereby permitting fluid ejected from the first outlet to be predominantly ejected out of the third outlet relative to the second outlet.

The various aspects of the various embodiments may be used alone or in any combination, as is desired.

BRIEF DESCRIPTION OF THE DRAWINGS

FIGS. 10A-10D are partial perspective views of the distal section of a device for delivering fluid to a nasal cavity having an alignment tab and landing surfaces, according to embodiments.

DETAILED DESCRIPTION

Figure 1:
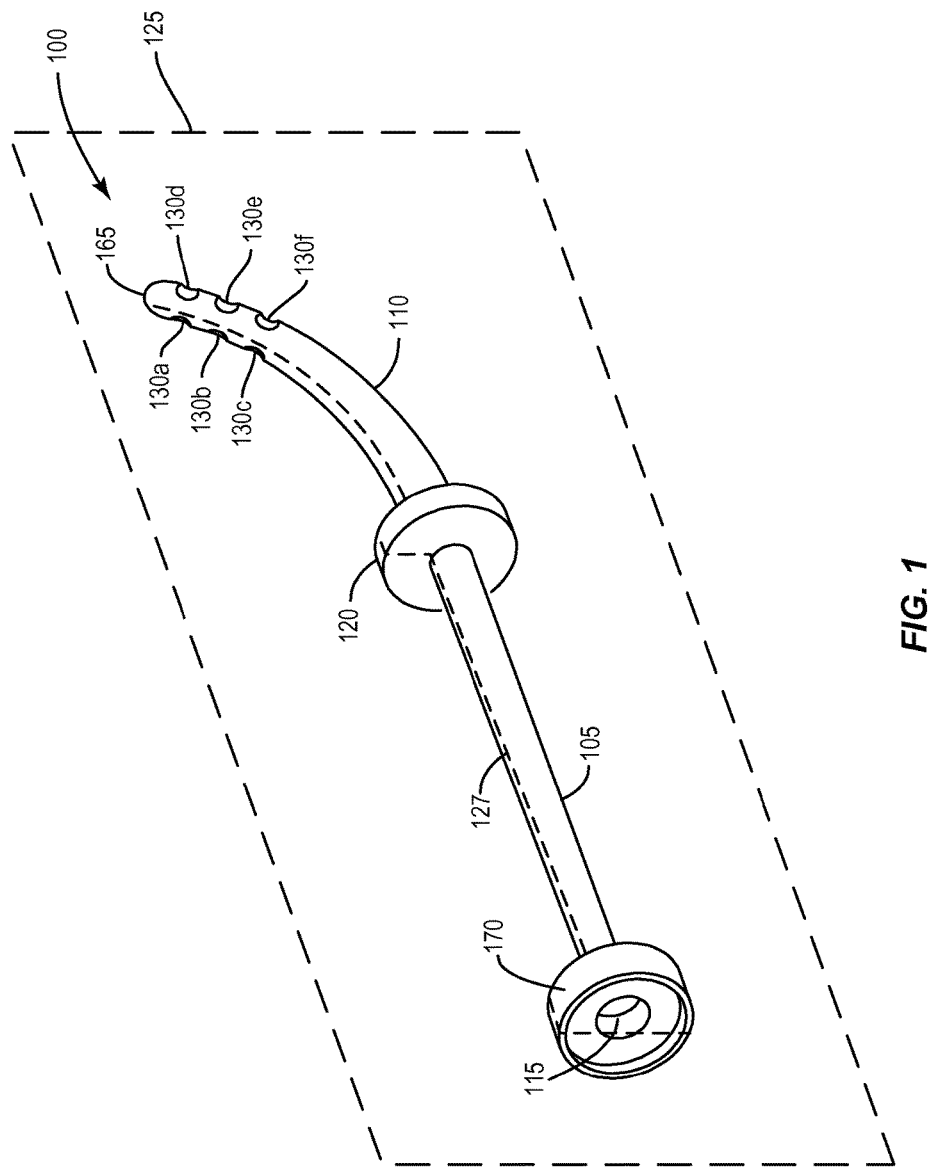
FIG. 1 is a perspective view of a device for delivering fluid to a nasal cavity, according to embodiments.

FIG. 1 depicts a device 100 for delivering fluid to a nasal cavity. The device 100 comprises an elongated member comprising a hollow exterior cannula 110 and a hollow interior cannula 105. The interior cannula 105 comprises an inlet 115 through which fluid to be delivered to the nasal cavity is supplied to the device 100. The inlet 115 comprises a mating adapter 170 so that a separate fluid dispensing source can be docked to the interior cannula 105 in order to supply the fluid. The interior cannula 105 is at least partially housed within the exterior cannula 110. The exterior cannula 110 has six outlets 130 for ejecting the supplied fluid into the nasal cavity. Although the embodiment of device 100 depicted in FIG. 1 has six outlets 130 in the outer cannula 110, other embodiments of the device 100 may have more outlets 130, or as few as two outlets 130, in the outer cannula 110. Further, although device 100 is depicted as comprising a mating adapter, other embodiments of the device 100 may omit this mechanism for docking with the separate fluid dispensing source.

The outlets 130 of the exterior cannula 110 are positioned within the nasal cavity by inserting the distal end 165 of the device 100 through a given nostril and continuing to insert the device 100 until the outlets 130 have also passed through the given nostril and into the nasal cavity. To facilitate ease of insertion, a portion of the device 100 has a curving centerline. The curve of this centerline lies along a geometric plane 125 that, for purposes of illustrating the positioning of the outlets 130 of the exterior cannula 110, divides the device 100 into a first and second lateral section along dividing line 127. The center of each of the outlets 130a-c are positioned in the first lateral section, and the center of each of the outlets 130d-f are positioned in the second lateral section. Although the embodiment of device 100 depicted in FIG. 1 has an exterior cannula 110 with three outlets 130 in each lateral section, according to other embodiments of the device 100, each lateral section of the exterior cannula 110 may have more than three outlets 130, or as few as one outlet 130, with a respective center positioned therein. Further, although the device 100 depicted in FIG. 1 has an exterior cannula 110 with outlets 130a-c positioned symmetrically to outlets 130d-f with respect to the plane 125, according to other embodiments of the device 100, the outlets 130 may be asymmetrically positioned with respect to the plane 125.

Device 100 also comprises a depth stop 120 connected to the exterior cannula 110. The depth stop 120 is larger in diameter than the exterior cannula 110, thereby effectively preventing over-insertion of the distal end 165 into the nasal cavity.

Figure 2:
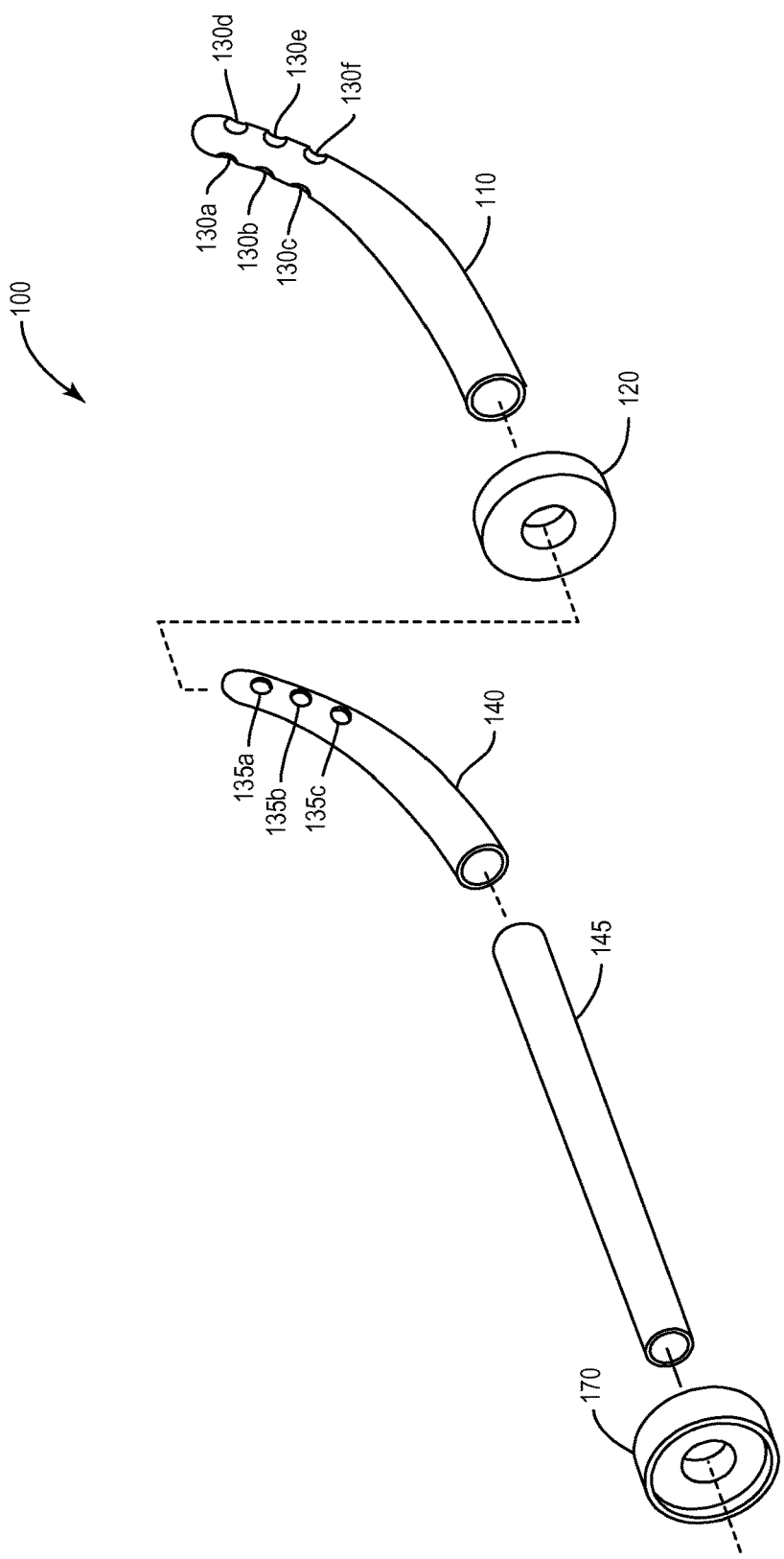
FIG. 2 is an exploded view of a device for delivering fluid to a nasal cavity, according to embodiments.

FIG. 2 is an exploded view of the device 100. The device 100 includes, an interior cannula 105 (not labeled in FIG. 2) comprising a mating adapter 170, a shaft 145, and a distal section 140. The mating adapter 170 is at the proximal end of the device 100 and is for mating with the fluid dispensing source, such as a spray bottle or syringe. The mating adapter 170 connects to the shaft 145 to form an inlet 115 at the proximal end (not labeled in FIG. 2). The shaft 145 of the interior cannula 105 connects to the distal section 140 of the interior cannula 105. The distal section 140 has three outlets 135a-c. Each outlet 135a-c is in fluid-flow relationship with the inlet 115 via the shaft 145. Although the embodiment of device 100 depicted in FIG. 2 has three outlets 135a-c, other embodiments of the device 100 may have more outlets 135, or as few as one outlet 135.

Although the distal section 140 is depicted in FIG. 2 as having a continuous curve throughout, according to embodiments, only a portion of the distal section 140 of the interior cannula 105 is curved. Further, according to embodiments, the rate of curve may be constant, may increase, or may decrease throughout the curve. In addition, embodiments of the device 100 have a distal section 140 of the interior cannula 105 that is flexible relative to the exterior cannula 110. Other embodiments of the device 100 have an interior cannula 105 with a distal section 140 that is so flexible that the curve of the distal section 140 is supported and maintained by the relatively more rigid exterior cannula 110 in which the distal section 140 is housed. Other embodiments have a distal section 140 that is malleable, but is able to retain the curve even without the support of the exterior cannula 110. Notwithstanding, the distal section 140 permits the outlets 135a-c to be selectively positionable into various orientations by rotation of the distal section 140 of the interior cannula 105 within the exterior cannula 110. Further, although the embodiment of device 100 depicted in FIG. 2 shows the interior cannula 105 in pieces, other embodiments of the device 100 may have an interior cannula 105 that is a single piece.

The interior cannula 105 passes through the depth stop 120 and into the exterior cannula 110. The depth stop 120 may be attached to the interior cannula 105 or the exterior cannula 110 as a separate piece, or as a single piece, according to embodiments. The exterior cannula 110 has outlets 130a-f. Each of outlets 130a-c, and outlets 130d-f, are arranged in similar configuration to the outlets 135a-c of the interior cannula 105, such that the outlets 135a-c of the interior cannula 105 can be rotated to predominantly face either outlets 130a-c or outlets 130d-f.

Figure 3:
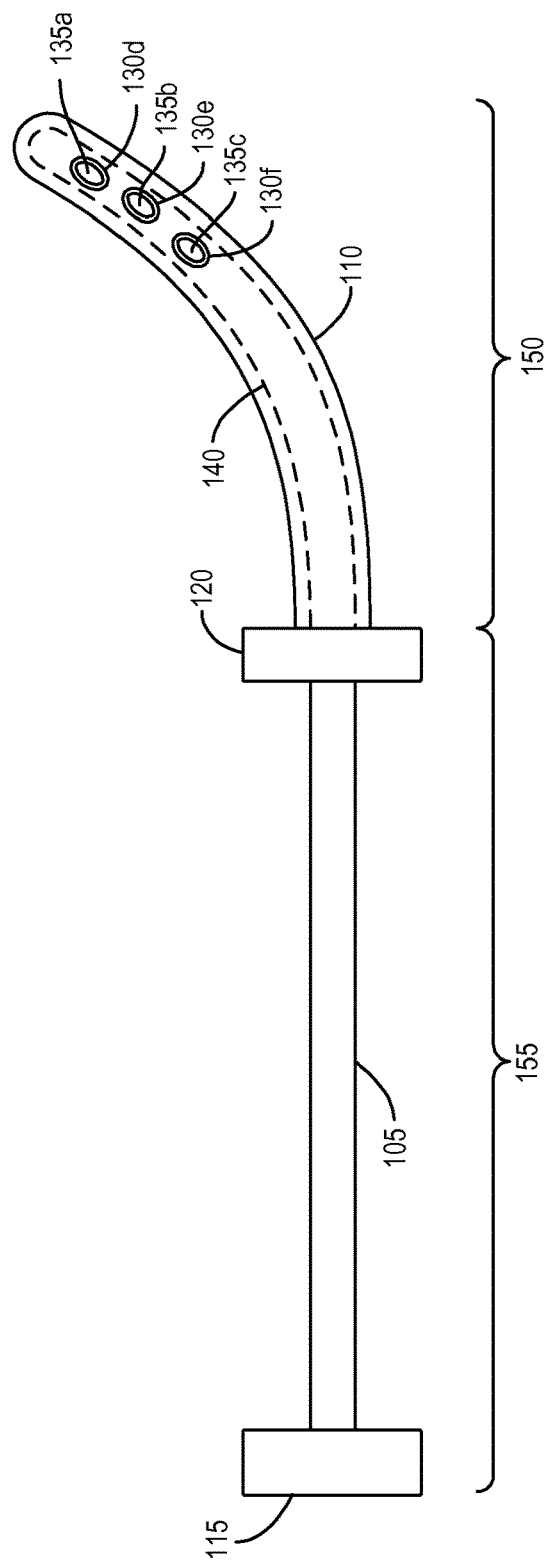
FIG. 3 is a schematic view of a device for delivering fluid to a nasal cavity, according to embodiments.

FIG. 3 schematically illustrates the device 100 as viewed from the second lateral side. The device 100 is axially divided into a distal section 150 and a proximal section 155. FIG. 3 also schematically illustrates the distal section 140 of the interior cannula 105 housed within the exterior cannula 110. FIG. 3 further illustrates the outlets 135a-c of the interior cannula 105 and outlets 130d-f of the exterior cannula. The relative positioning of outlets 135a-c on the distal section 140 of the interior cannula 105 is similar to the relative positioning of the outlets 130d-f of the exterior cannula 110. Although not depicted in FIG. 3, the relative positioning of outlets 135a-c is also similar to the relative positioning of the outlets 130a-c on the first lateral side of the exterior cannula 110.

Figure 4A:
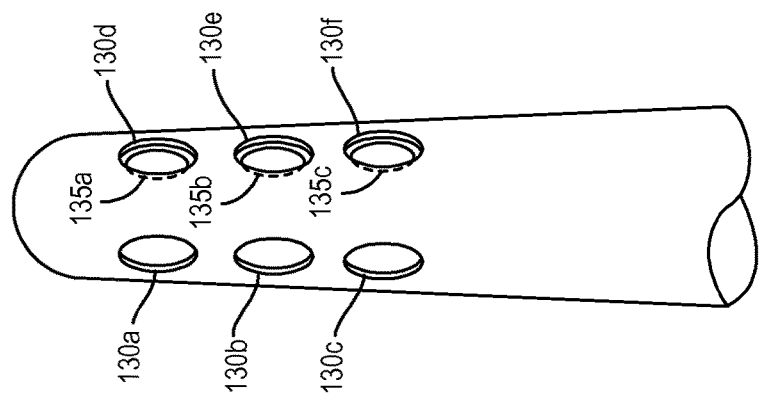
FIGS. 4A-B are partial perspective views of the distal section of a device for delivering fluid to a nasal cavity with outlets positioned in a first and second orientation, according to embodiments.

FIG. 4A shows the outlets 135a-c of the interior cannula 105 (not labeled in FIG. 4A) selectively positioned in a first orientation. In the first orientation, the outlets 135a-c of the interior cannula 105 are in closer proximity to the outlets 130a-c on the first lateral side of the exterior cannula 110 than to the outlets 130d-f on the second lateral side of the exterior cannula 110. The first orientation thereby permits fluid ejected from the outlets 135a-c of the interior cannula 105 to be predominantly ejected out of the outlets 130a-c on the first lateral side of the exterior cannula 110 relative to the outlets 130d-f on the second lateral side of the exterior cannula 110.

Figure 4B:
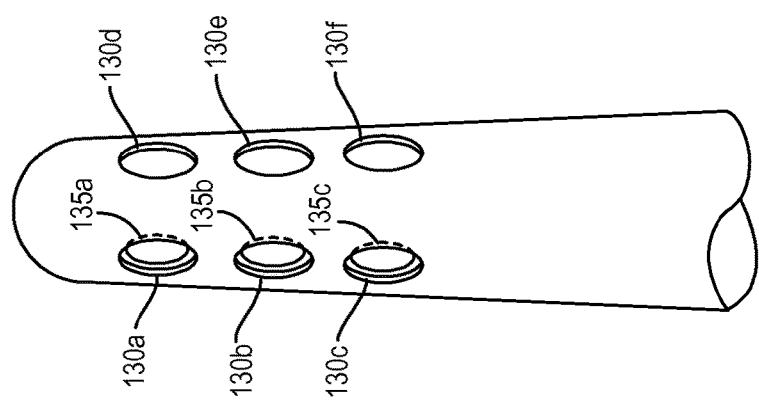

FIG. 4B shows the outlets 135a-c of the interior cannula 105 (not labeled in FIG. 4B) selectively positioned in a second orientation. In the second orientation, the outlets 135a-c of the interior cannula 105 are in closer proximity to the outlets 130d-f on the second lateral side of the exterior cannula 110 than to the outlets 130a-c on the first lateral side of the exterior cannula 110. The second orientation thereby permits fluid ejected from the outlets 135a-c of the interior cannula 105 to be predominantly ejected out of the outlets 130d-f on the second lateral side of the exterior cannula 110 relative to the outlets 130a-c on the first lateral side of the exterior cannula 110. The outlets 135a-c are selectively positionable into the first and second orientation by rotation of the distal section 140 of the interior cannula 105 within the exterior cannula 110.

Figure 5:
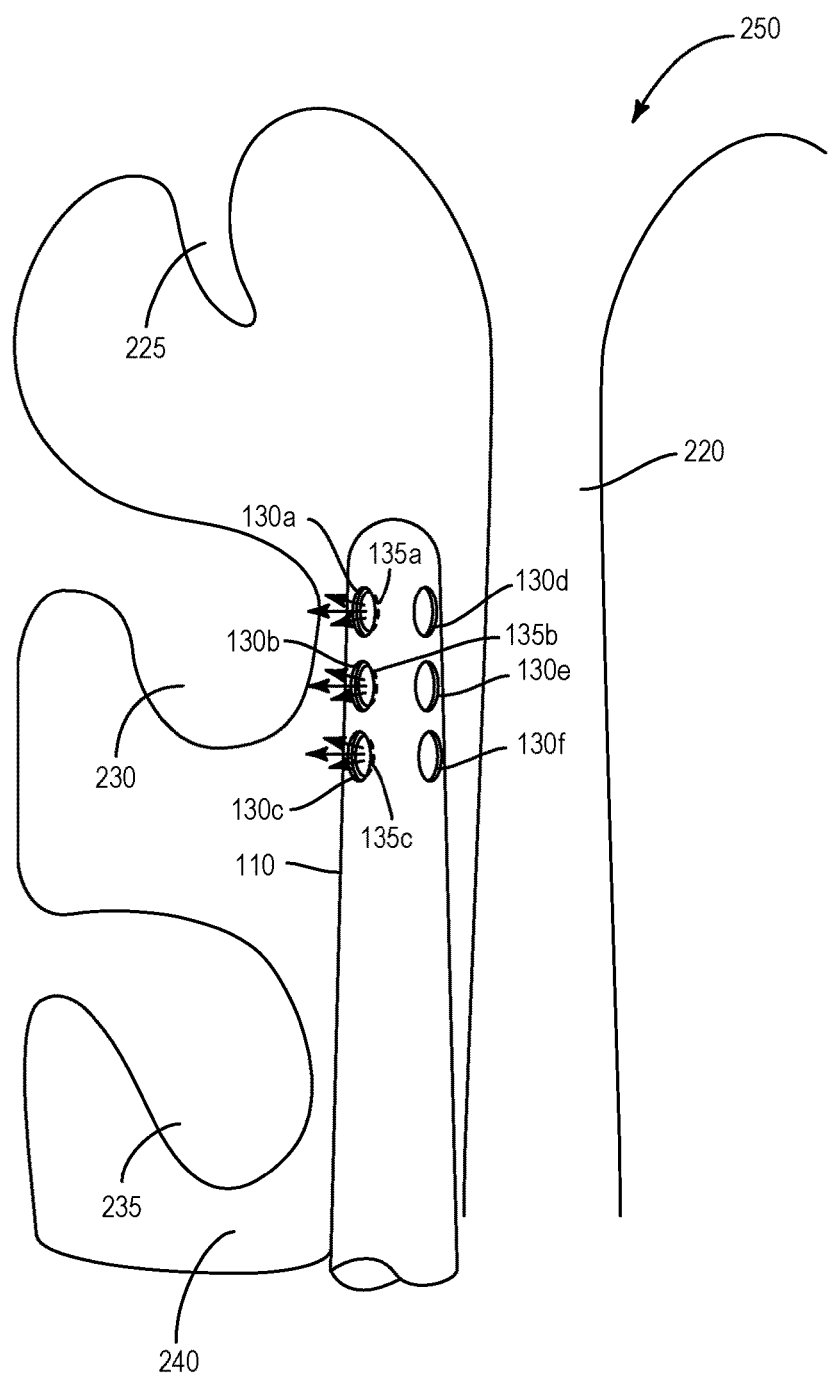
FIG. 5 is a schematic view of a nasal cavity in which a device for delivering fluid to a nasal cavity according to embodiments has been inserted.

FIG. 5 shows the distal section 150 of the device 100 inserted into the nasal cavity 250 through a nostril 240. The nasal cavity 250 is divided by the septum 220. The septum 220 is depicted on the second lateral side of the distal section 150. Opposing the septum 220, on the first lateral side of the distal section 150, are a superior turbinate 225, a middle turbinate 230, and an inferior turbinate 235 of the nasal cavity 250. The extent of insertion into the nostril 240 may be limited by the depth stop 120 (not shown in FIG. 5) contacting the exterior of the nostril 240.

The outlets 135a-c of the interior cannula 105 are positioned in the first orientation. In one embodiment, the distal section 150 is four centimeters long and has a continuous curve of seventy degrees, such that outlets 130a-c on the first lateral side of the exterior cannula 110 are brought in close proximity to the middle turbinate 230. The close positioning of the outlets 130a-c on the first lateral side of the exterior cannula 110, and the positioning of outlets 135a-c of the interior cannula in the first orientation, permit fluid ejected from the device 100 to be directly and efficiently applied to the middle turbinate 230 without wastefully delivering fluid to other surfaces within the nasal cavity 250.

The device 100 may have a longer or shorter distal section 150 as appropriate, depending on which surface of the nasal cavity 250 requires the delivery of fluid, the anatomy of the particular patient, the age of the patient, and so on. When delivery of fluid to the middle turbinate 230 is desired, for a typical adult patient, an embodiment of the device 100 having a distal section 150 of between 3.75 and 4.25 centimeters may be most suitable. When delivery of fluid is desired to surfaces other than the middle turbinate 230 (e.g., the superior turbinate 225, the inferior turbinate 235), or if the patient is anatomically different from a typical adult patient (e.g., a child, a trauma victim), a device 100 having a distal section 150 between 3 and 5 centimeters may be appropriate.

The device 100 may have a distal section 150 that curves to a lesser or greater degree as appropriate, depending on which surface of the nasal cavity 250 requires the delivery of fluid, the anatomy of the particular patient, the age of the patient, and so on. When delivery of fluid to the middle turbinate 230 is desired, for a typical adult patient, an embodiment of the device 100 having a distal section 150 of between sixty-seven and seventy-three degrees of curvature may be most suitable. When delivery of fluid is desired to surfaces other than the middle turbinate 230 (e.g., the superior turbinate 225, the inferior turbinate 235), or if the patient is anatomically different from a typical adult patient (e.g., a child, a trauma victim), a device 100 having a distal section 150 of between sixty and eighty degrees of curvature may be appropriate.

Further, although FIG. 5 depicts the outlets 135a-c of the interior cannula 105 in the first orientation, the outlets 135a-c may also be selectively positioned in the second orientation in order to deliver fluid to the septum 220. Such may be desired, for example, to deliver blood coagulant to a cut or lesion of the flesh surrounding the septum 220. Further still, while FIG. 5 depicts only one side of the nasal cavity 250, the device 100 may also be inserted into the nostril 240 on the opposite side of the septum 220, with the outlets 135a-c of the interior cannula 105 in either the first or second orientation in order to deliver fluid to the septum 220 or to a turbinate, respectively, as desired.

Figure 6:
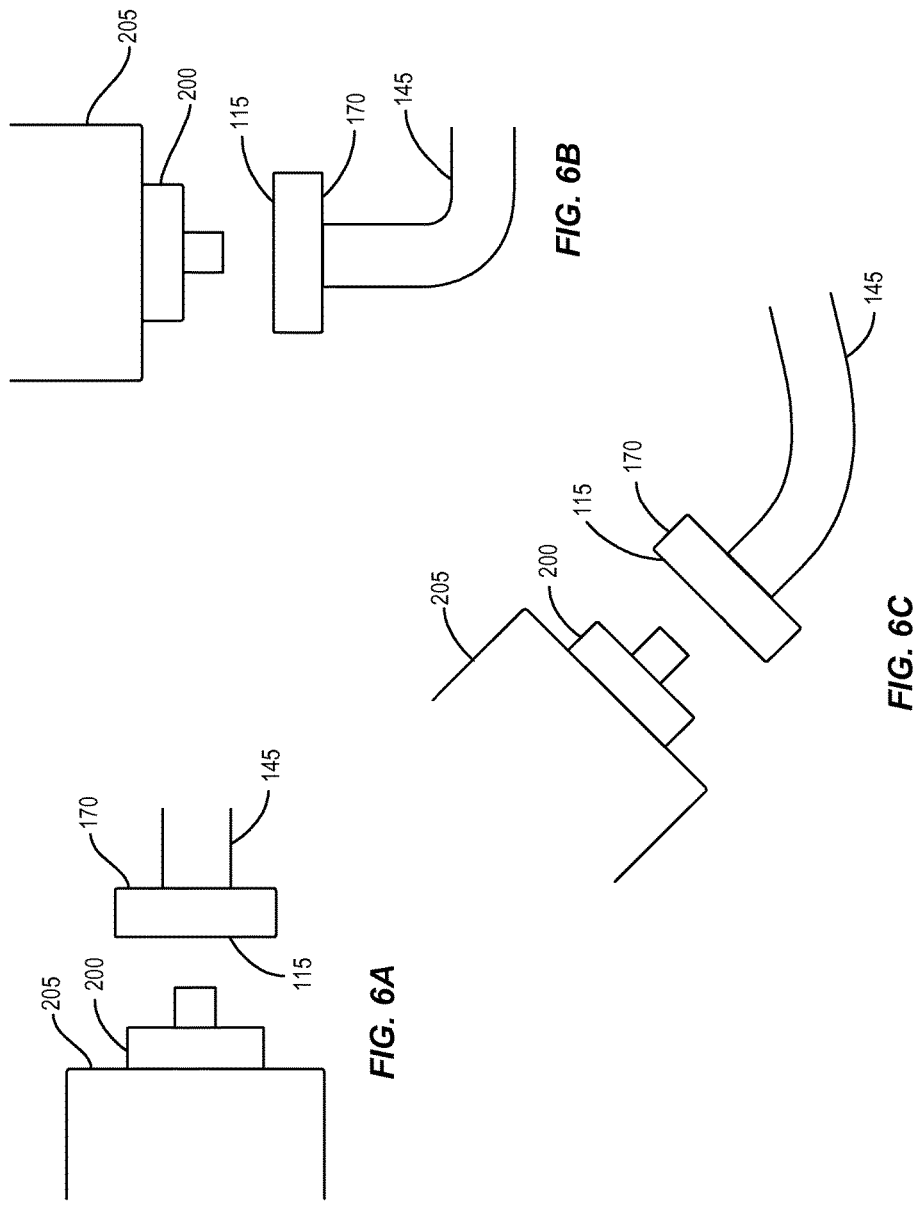
FIGS. 6A-6C are partial perspective views of the proximal section of a device for delivering fluid to a nasal cavity docking with a fluid-retention chamber, according to embodiments.

The fluid may be stored in a separate fluid-retention chamber 205 (e.g., a nasal spray bottle, a syringe) that retains the fluid until the fluid is to be used. Such a fluid-retention chamber 205 may comprise a nozzle 200 for dispensing the fluid. FIGS. 6A-C illustrate different ways that a fluid-retention chamber 205 can be mated to the proximal end of the interior cannula 105 in order to supply the device 100 with fluid. According to embodiments, the shaft 145 of the interior cannula may be straight (as illustrated in FIG. 6A), bent sharply (as illustrated in FIG. 6B), or bent gently (as illustrated in FIG. 6C) so that the inlet 115 presents a mating surface that can accommodate fluid-retention chambers 205 and nozzles 200 of differing dimensions and specifications. In the examples depicted in FIGS. 6A-C, the fluid-retention chamber 205 comprises a nozzle 200 that can be mated to the inlet 115. As discussed previously, the inlet 115 comprises a mating adapter 170, according to embodiments, for easily mating with the fluid-retention chamber 205. The mating adapter 170 may also guide the nozzle 200 into the inlet 115 during mating, and form a seal with the nozzle 200 in order to prevent the fluid from leaking out of the inlet while the fluid is being supplied to the device 100.

Figure 7:
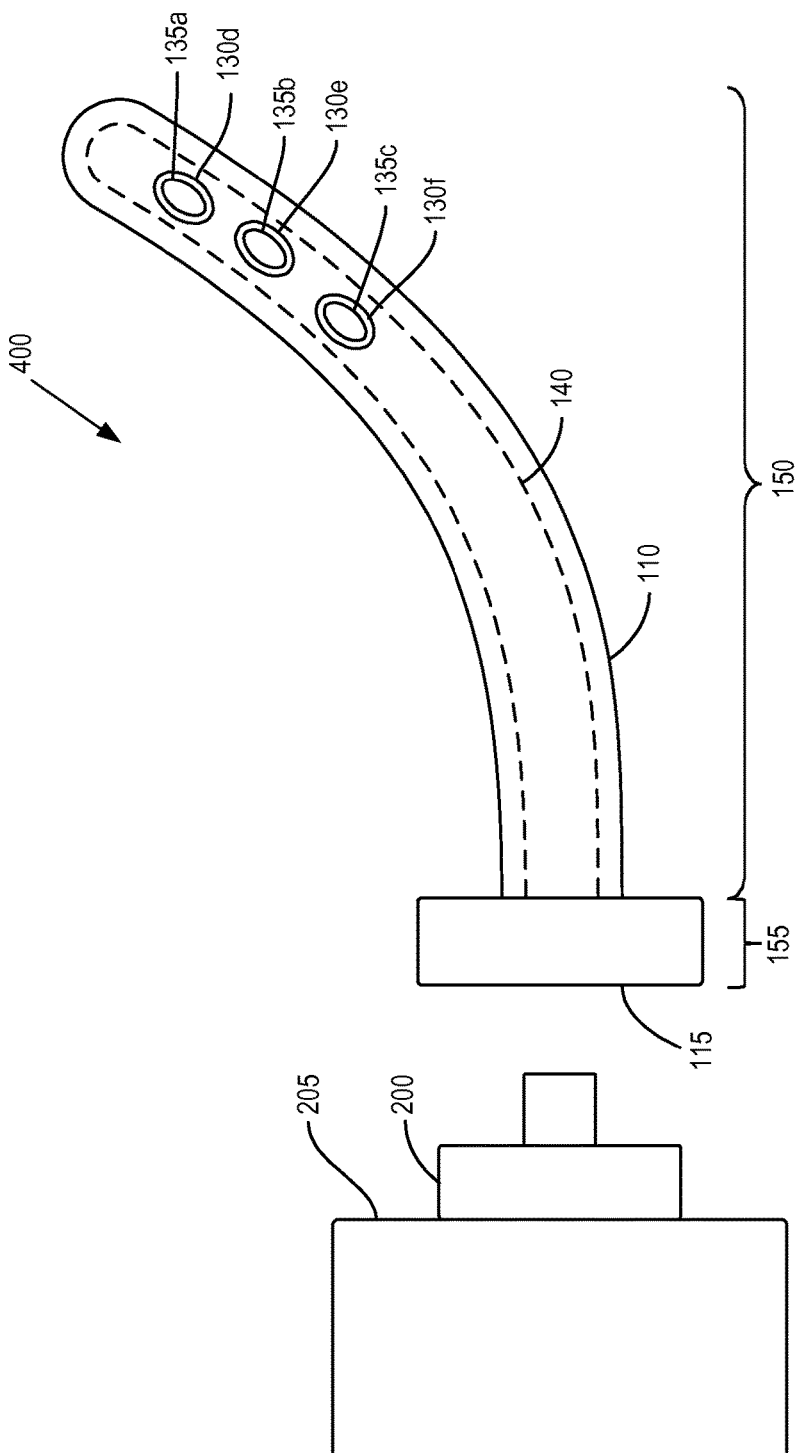
FIG. 7 is a schematic view of a device for delivering fluid to a nasal cavity having an abbreviated proximal section, according to embodiments.

FIG. 7 illustrates a different embodiment of a device 400 for delivering fluid to the nasal cavity that has an abbreviated proximal section 155 comprising only the inlet 115 of the interior cannula 105. Thus, interior cannula 105 omits the shaft 145. Instead, the distal section 140 of the interior cannula 105 connects directly to the inlet 115. The inlet 115 is able to mate with the fluid retention chamber 200 and nozzle 205. The inlet 115 also functions as a depth stop 120 to prevent over-insertion of the device 400 into the nasal cavity 250 (not illustrated in FIG. 7). The inlet 115 is further connected to the exterior cannula 110. The outlets 135a-c in the distal section 140 of the interior cannula 105 are selectively positionable by rotation into the first and second orientation as previously discussed.

Figure 8:
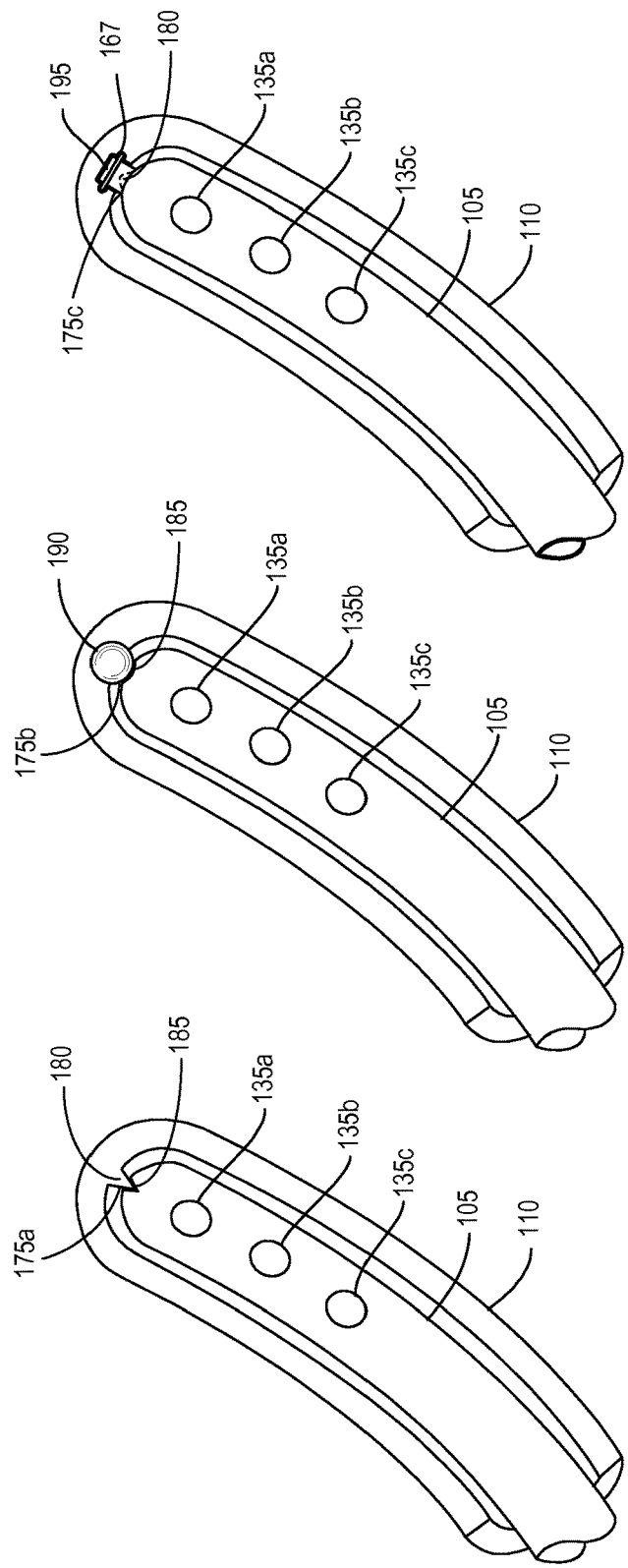
FIGS. 8A-8C are partial perspective views of a device for delivering fluid to the nasal cavity that implement a rotating joint, according to embodiments.

FIGS. 8A-C illustrate further embodiments of the device 100 in which the exterior cannula 110 and interior cannula 105 connect at a rotating joint 175 such that the distal end of the interior cannula 105 is kept substantially centered within the distal section of the exterior cannula 110. FIG. 8A depicts a rotating joint 175a in which a protrusion 180 from an interior surface of the exterior cannula 110 contacts a detent 185 in the exterior surface of the interior cannula 105, such that lateral forces applied to the interior cannula 105 during rotation are generally inadequate to dislodge the protrusion 180 from the detent 185. FIG. 8B depicts a rotating joint 175b in which a rolling ball 190 is housed within the distal end of the exterior cannula 110. The rolling ball 190 contacts a detent 185 in the exterior surface of the interior cannula 105, such that lateral forces applied to the interior cannula 105 during rotation are generally inadequate to dislodge the rolling ball 190 from the detent 185. FIG. 8C depicts a rotating joint 175c in which a rotating cylinder 195 is housed within the distal end of the exterior cannula 110. The rotating cylinder 195 is retained in the distal end of the exterior cannula 110 by a tongue 167 protruding from the rotating cylinder 195 that slides along a groove of the exterior cannula 110. The rotating cylinder 195 accepts a protrusion 180 from the interior cannula 105 and guides the center of the distal end of the interior cannula 105 toward the center of the distal end of the exterior cannula 110. The contact between the rotating cylinder 195 and the protrusion 180 in the exterior surface of the interior cannula 105 are such that lateral forces applied to the interior cannula 105 during rotation are generally inadequate to dislodge the protrusion 180 from the rotating cylinder 195.

Figure 9:
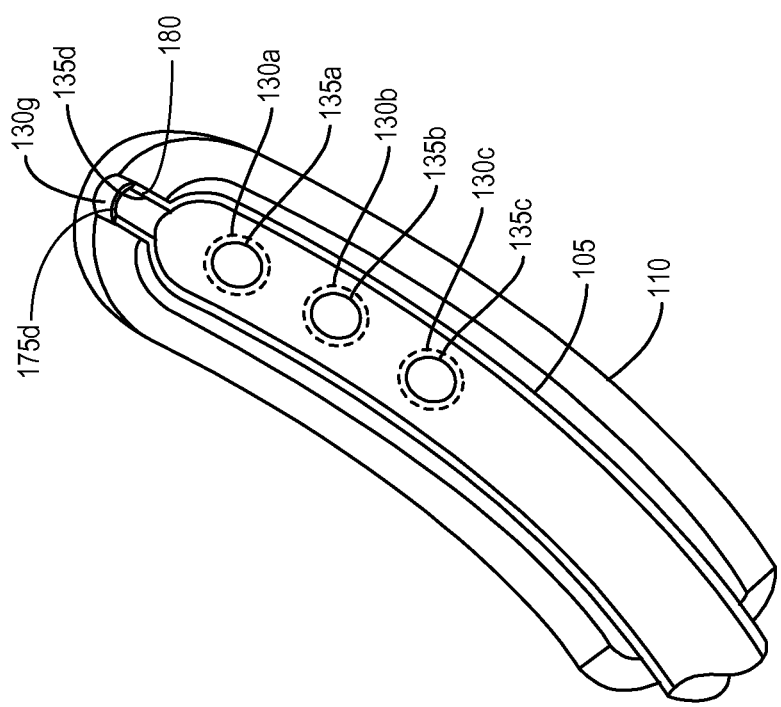
FIG. 9 is a partial perspective view of the distal section of a device for delivering fluid to a nasal cavity having outlets at the distal end, according to embodiments.

FIG. 9 illustrates a further embodiment of the device 100 in which the interior cannula 105 has an outlet 135d, and the exterior cannula 110 has an outlet 130g, in the distal end. According to embodiments, a protrusion 180 from the exterior surface around the outlet 135d of the interior cannula 105 fits within the outlet 130g of the exterior cannula 110 to form a rotating joint 175d. The outlet 135d is in fluid-flow relationship with the inlet 115 (not shown in FIG. 9), such that fluid may be ejected from the distal end when the outlets 135a-c are positioned in either the first or second orientation.

Because the distal end 140 of the interior cannula 105 is housed within the exterior cannula 110, it may be difficult to visually determine when the outlets 135a-c are in the first orientation or the second orientation, according to various embodiments of the device 100. FIGS. 10A-D illustrate various ways to assist a user in selectively positioning the outlets 135a-c into the first and second orientations without having to visually identify where the outlets 135a-c are positioned within the exterior cannula 110. According to the embodiment of FIG. 10A, an alignment tab 160 protrudes from an interior surface of the exterior cannula 110. The interior cannula 105 has a first landing surface 165a and a second landing surface 165b. Upon rotation of the interior cannula 105 to position the outlets 135a-c of the interior cannula 105 into the first orientation, the alignment tab 160 contacts the first landing surface 165a. Upon rotation of the interior cannula 105 to position the outlets 135a-c of the interior cannula 105 into the second orientation, the alignment tab 160 contacts the second landing surface 165b. The user is able to tactilely feel when the alignment tab 160 makes contact with either of the alignment surfaces 165a, 165b and thereby knows that the outlets 135a-c of the interior cannula 105 are in either the first or second orientation.

FIG. 10B also depicts an alignment tab 160 protruding from an interior surface of the exterior cannula 110. The interior cannula 105 also has a first landing surface 165a and a second landing surface 165b. However, according to the embodiment of FIG. 10B, the alignment tab 160 and landing surfaces 165a, 165b are shaped to directly oppose each other upon contact, such that the interior cannula 105 is blocked from being rotated to position the outlets 135a-c beyond the first orientation at one extreme, and the second orientation at the opposite extreme.

Figure 10D:
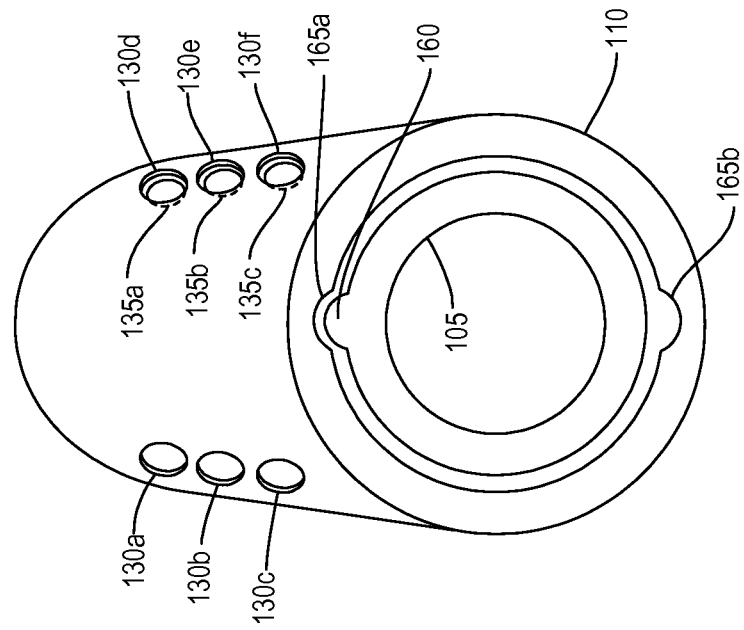
Figure 10C:
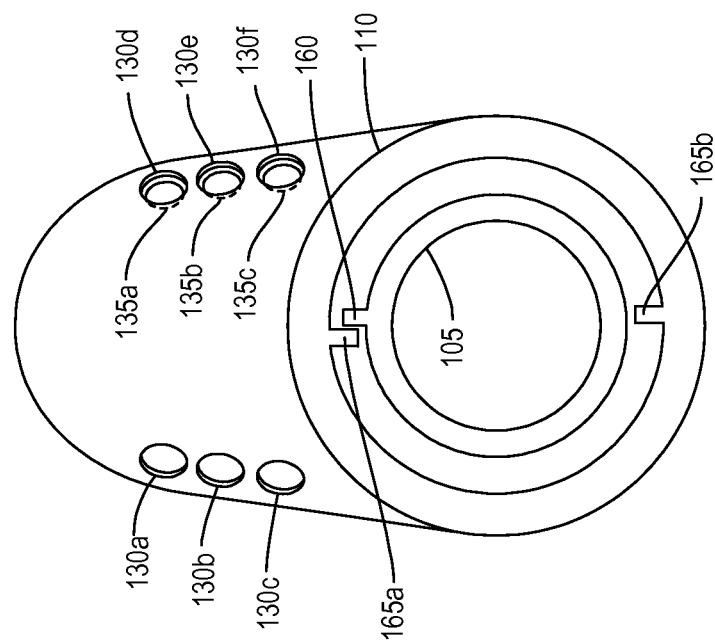

In the embodiments of FIGS. 10C-D, the alignment tab 160 protrudes from an exterior surface of the interior cannula 105, and the interior surface of the exterior cannula has a first landing surface 165a and a second landing surface 165b. In the embodiment illustrated in FIG. 10C, the alignment tab 160 and landing surfaces 165a, 165b are again shaped to directly oppose each other upon contact, such that the interior cannula 105 is blocked from being rotated to position the outlets 135a-c beyond the first orientation at one extreme, and the second orientation at the opposite extreme. This is in contrast to the embodiment of FIG. 10D which permits complete rotation of the interior cannula 105, and merely allows a user to tactilely feel when the alignment tab 160 contacts a landing surface 165a, 165b.

Figure 11:
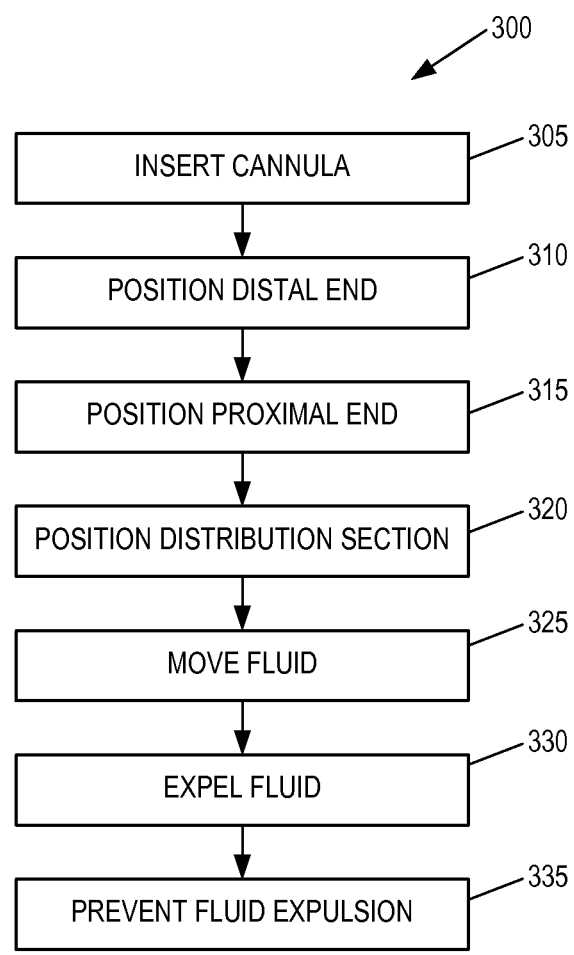
FIG. 11 illustrates an exemplary method for delivering fluid to a nasal cavity, according to embodiments.

FIG. 11 illustrates one possible method 300 of delivering fluid to a nasal cavity 250. The nasal cavity 250 comprises a first set of turbinates corresponding to a first nostril and a second set of turbinates corresponding to a second nostril. Each set of turbinates comprises an inferior 235, middle 230, and superior turbinate 225. The first set of turbinates and first nostril are separated from the second set of turbinates and second nostril by the septum 220. The method comprises inserting an elongated cannula 105 through a given nostril 240 and into the nasal cavity 250 in a first direction (block 305), thereby positioning a distal end of the cannula 105 in the nasal cavity 250 (block 310), a proximal end of the cannula 105 exterior to the nasal cavity 250 (block 315), and one or more outlets 135 of a distribution section of the cannula 110 in the nasal cavity 250, such that the one or more outlets 130 predominantly face away from the septum 220 and toward the set of turbinates corresponding to the given nostril 240, the distribution section of the cannula being positioned away from the distal end of the cannula 105 (block 320). The method 300 further comprises moving fluid into an inlet 115 at the proximal end and along the cannula 105 while the cannula is in the nasal cavity 250 (block 325), and expelling fluid from the distribution section of the cannula 105 in a direction predominantly transverse to the first direction, thereby delivering the expelled fluid to at least one of the turbinates in the set of turbinates corresponding to the given nostril 240 (block 335).

To deliver the expelled fluid to at least one of the turbinates in the set of turbinates corresponding to the given nostril 240 (block 335), the method 300 may comprise delivering the fluid predominantly to the middle turbinate 230 relative to the inferior 235 and superior turbinates 225. Embodiments of the method 300 may also include either expelling the fluid (block 330) from the distal end of the cannula 105, or preventing fluid from being expelled from the distal end of the cannula 105 while fluid is being expelled from the distribution section (block 335). Further, embodiments of the method 300 may also include preventing fluid from being expelled from the cannula 105 towards the septum 220 while fluid is being expelled from the distribution section (block 325).

The present invention may be carried out in other ways than those specifically set forth herein without departing from the essential characteristics of the invention. The present embodiments are to be considered in all respects as illustrative and not restrictive, and all changes coming within the meaning and equivalency range of the appended claims are intended to be embraced therein.

Although the present disclosure has been discussed in terms of a nasal cavity that would be typically be found in a human adult, embodiments of the present disclosure can similarly be used to deliver fluid to the nasal cavity of non-humans (e.g., animals) and children.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

What is claimed is:

1. A device for delivering fluid to a nasal cavity, the device comprising:
    an elongated member comprising a hollow exterior cannula and a hollow interior cannula;
    the elongated member and interior cannula each including a proximal section that extends away from a proximal end and a distal section that extends from the proximal section;
    the exterior cannula and the interior cannula both comprising a closed distal end;
    the interior cannula being housed within the exterior cannula throughout the distal section of the elongated member;
    the distal section of the elongated member having a centerline comprising a curve that extends in a plane dividing the distal section of the elongated member into a first lateral section and a second lateral section;
    the interior cannula including an inlet at the proximal end of the interior cannula in fluid-flow relationship to a first outlet along the distal section of the interior cannula, the first outlet opening into the exterior cannula;

the exterior cannula including, along a distal section of the exterior cannula:
  a second outlet having a center in the first lateral section; and
  a third outlet having a center in the second lateral section;

the first outlet being selectively positionable into a first and second orientation by rotation of the interior cannula relative to the exterior cannula;

the first orientation comprising the first outlet in closer proximity to the second outlet than to the third outlet, thereby permitting fluid ejected from the first outlet to be predominantly ejected out of the second outlet relative to the third outlet;

the second orientation comprising the first outlet in closer proximity to the third outlet than to the second outlet, thereby permitting fluid ejected from the first outlet to be predominantly ejected out of the third outlet relative to the second outlet.

2. The device of claim 1, wherein the second outlet is positioned symmetrically to the third outlet with respect to the plane.

3. The device of claim 1, wherein the distal section of the elongated member is between three and five centimeters long, and the curve has between sixty and eighty degrees of curvature.

4. The device of claim 3, wherein the distal section of the elongated member is between 3.75 and 4.25 centimeters long, and the curve has between sixty-seven and seventy-three degrees of curvature.

5. The device of claim 1, wherein the distal section of the interior cannula is flexible relative to the exterior cannula to permit the rotation of the interior cannula within the exterior cannula, and such that the exterior cannula maintains a curve of the distal section of the interior cannula during the rotation.

6. The device of claim 1, wherein the exterior cannula and the interior cannula connect at a rotating joint in which a first element at the distal end of the exterior cannula contacts against a second element at the distal end of the interior cannula such that the distal end of the interior cannula is kept centered within the distal end of the exterior cannula during the rotation of the interior cannula relative to the exterior cannula.

7. The device of claim 1:
wherein the interior cannula further comprises an alignment tab that protrudes from an exterior surface of the interior cannula;
wherein the exterior cannula further comprises:
  a first landing surface such that, upon rotation of the interior cannula to position the first outlet into the first orientation, the alignment tab contacts the first landing surface;
  a second landing surface such that, upon rotation of the interior cannula to position the first outlet into the second orientation, the alignment tab contacts the second landing surface.

8. The device of claim 1:
wherein the exterior cannula further comprises an alignment tab that protrudes from an interior surface of the exterior cannula;
wherein the interior cannula further comprises:
  a first landing surface such that, upon rotation of the interior cannula to position the first outlet into the first orientation, the alignment tab contacts the first landing surface;
  a second landing surface such that, upon rotation of the interior cannula to position the first outlet into the second orientation, the alignment tab contacts the second landing surface.

9. The device of claim 1, further comprising a depth stop, connected to the exterior cannula, for preventing more than the distal section of the elongated member from being inserted into the nasal cavity.

10. The device of claim 1:
wherein the interior cannula further includes at least one fourth outlet, each fourth outlet opening into the exterior cannula and being in fluid-flow relationship with the inlet;
wherein the exterior cannula further includes:
  at least one fifth outlet, each having a center in the first lateral section;
  at least one sixth outlet, each having a center in the second lateral section;
wherein the first orientation further comprises each fourth outlet in closer proximity to a respective fifth outlet than a respective sixth outlet, thereby permitting fluid ejected from each fourth outlet to be predominantly ejected out of the respective fifth outlet relative to the respective sixth outlet;
wherein the second orientation further comprises each fourth outlet in closer proximity to a respective sixth outlet than a respective fifth outlet, thereby permitting fluid ejected from each fourth outlet to be predominantly ejected out of the respective sixth outlet relative to the respective fifth outlet.

11. The device of claim 1, wherein the interior cannula further includes a shaft connecting the distal section of the interior cannula to the inlet at the proximal end of the interior cannula.

12. The device of claim 11, wherein the shaft comprises a bend.

13. The device of claim 1, wherein the inlet comprises a mating adapter for mating with a fluid-dispensing source.

14. A device, having a proximal section that extends away from a proximal end and a distal section that extends from the proximal section to a distal end, for delivering fluid to a nasal cavity, the device comprising:
a hollow interior cannula comprising an inlet at a proximal end of the interior cannula and a first outlet positioned in a distal section of the interior cannula, the inlet and the first outlet being in fluid-flow relationship;
a hollow exterior cannula housing at least the distal section of the interior cannula and comprising a second and third outlet in a distal section of the exterior cannula, the exterior cannula being stiff relative to the distal section of the interior cannula;
the interior cannula and the exterior cannula each comprising a closed distal end;
wherein the second outlet is on a first lateral side of the exterior cannula;
wherein the third outlet is on a second lateral side of the exterior cannula, the second lateral side opposing the first lateral side;
wherein the distal section of the exterior cannula has a centerline comprising a curve that extends in a plane dividing the first and second lateral sides;

the first outlet being selectively positionable into a first and second orientation by rotation of the distal section of the interior cannula within the exterior cannula;

the first orientation comprising the first outlet opening into the second outlet, thereby permitting fluid ejected from the first outlet to be predominantly ejected out of the second outlet relative to the third outlet;

the second orientation comprising the first outlet opening into the third outlet, thereby permitting fluid ejected from the first outlet to be predominantly ejected out of the third outlet relative to the second outlet.

* * * * *